(12) United States Patent
Vaidyaselvan

(10) Patent No.: US 8,851,892 B2
(45) Date of Patent: Oct. 7, 2014

(54) IMMEDIATE AND TEMPORARY DENTAL PROSTHESIS AND METHODS OF UTILIZING SAME

(76) Inventor: Ramalingam Vaidyaselvan, Marlboro, NJ (US)

( * ) Notice: Subject to any disclaimer, the term of this patent is extended or adjusted under 35 U.S.C. 154(b) by 1 day.

(21) Appl. No.: 13/149,228

(22) Filed: May 31, 2011

(65) Prior Publication Data
US 2012/0308959 A1 Dec. 6, 2012

(51) Int. Cl.
*A61C 13/12* (2006.01)
*A61C 13/225* (2006.01)

(52) U.S. Cl.
USPC .......................................................... 433/178

(58) Field of Classification Search
CPC ...... A61C 7/10; A61C 8/0033; A61C 8/0048; A61C 8/0057; A61C 8/0065
USPC ...................................... 433/7, 172–176, 178
See application file for complete search history.

(56) References Cited

U.S. PATENT DOCUMENTS

| 4,163,318 | A | * | 8/1979 | Tigani | 433/172 |
| 4,431,415 | A | * | 2/1984 | Tigani | 433/172 |
| 4,609,355 | A | * | 9/1986 | Harvey et al. | 433/181 |
| 4,661,067 | A | * | 4/1987 | Harvey et al. | 433/181 |
| 8,348,663 | B2 | * | 1/2013 | Maadi et al. | 433/7 |

* cited by examiner

*Primary Examiner* — Cris L Rodriguez
*Assistant Examiner* — Matthew Nelson
(74) *Attorney, Agent, or Firm* — Jon Fallon, Esq.; Michael P. Kochka, Esq.

(57) ABSTRACT

Embodiments of the present invention are generally related to embodiments of the present invention relate to a temporary dental prosthesis and methods of utilizing the same. More specifically, embodiments of the present invention relate to a dental prosthesis that may be quickly and easily set in a patient's mouth without the need for surgery or similar complex dental procedure. In one embodiment of the present invention, a temporary dental prosthesis comprises a primary body having a pair of axially positioned braces extending therefrom, the braces being connected to one another via an expansion means capable of extending and contracting the braces away from and towards the primary body, and an expansion control means for enabling the expansion means and controlling the expansion and contraction of the braces.

9 Claims, 8 Drawing Sheets

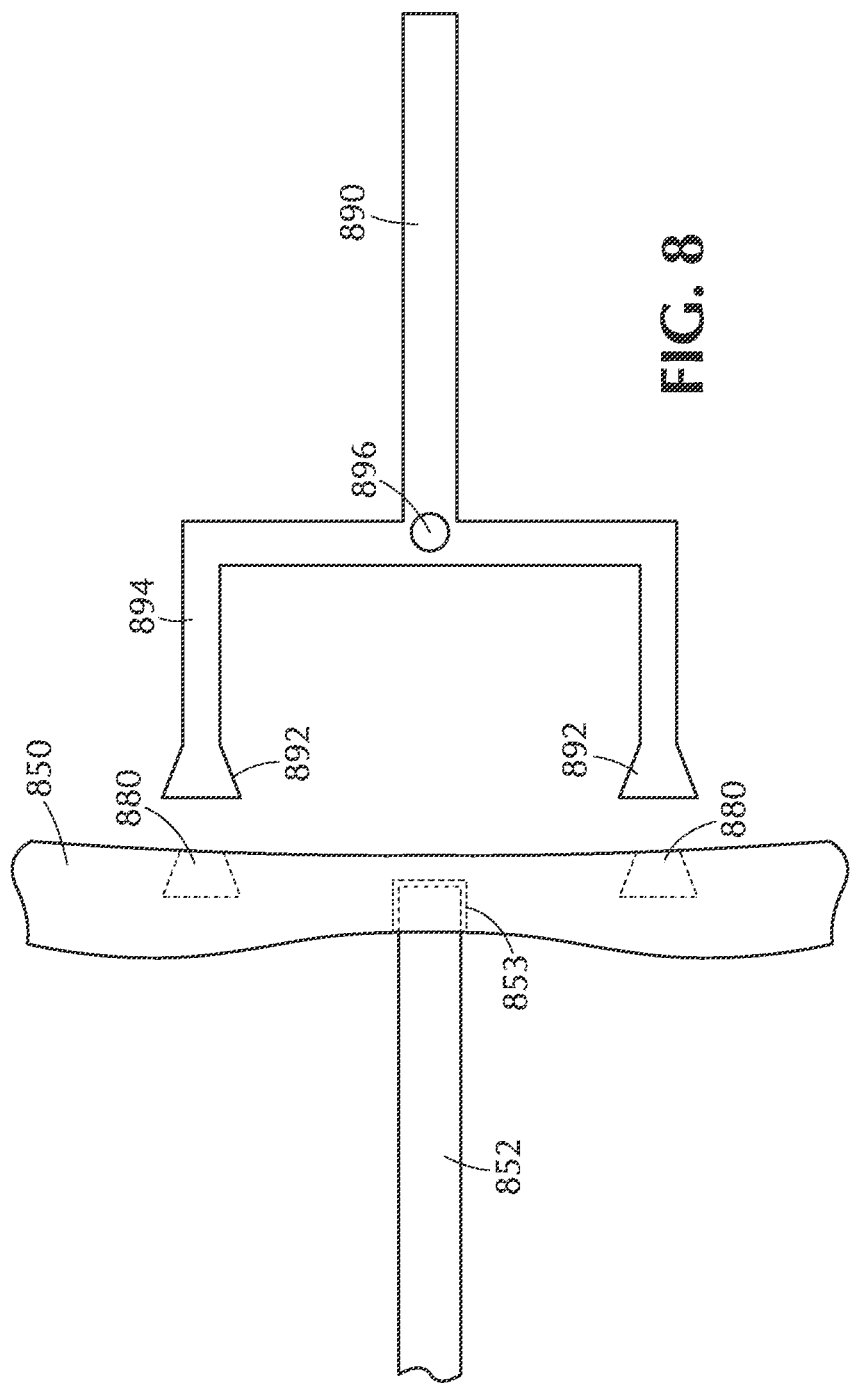

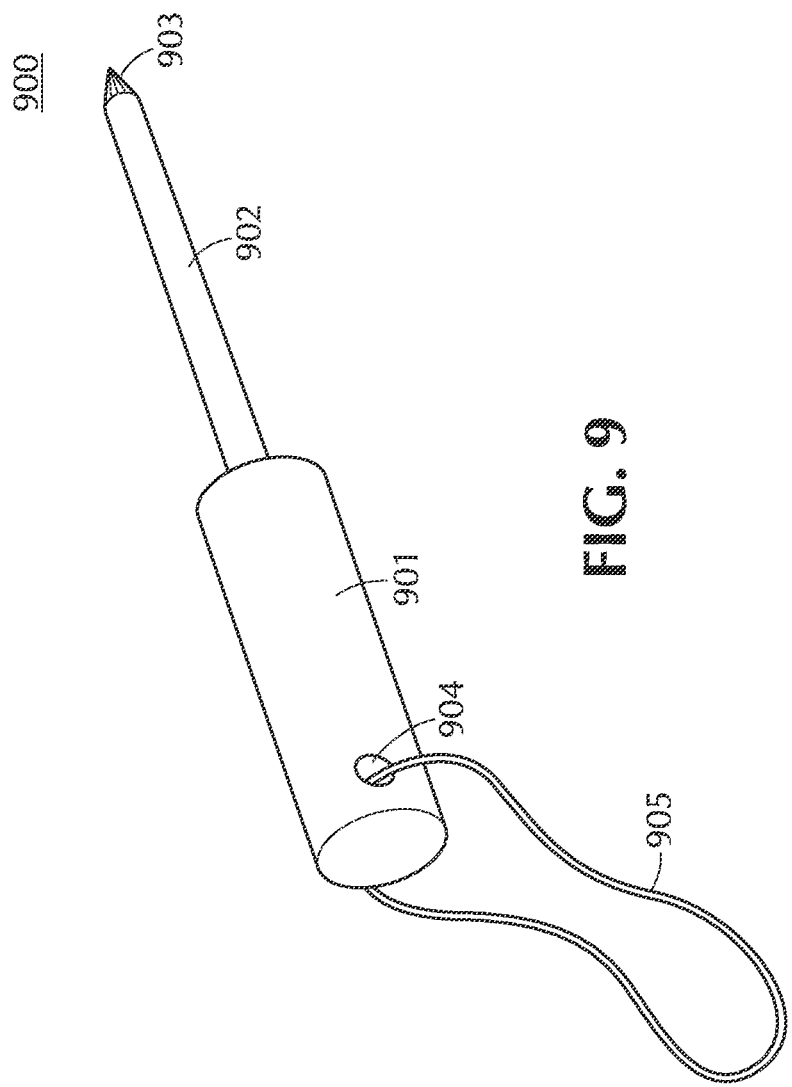

IMMEDIATE AND TEMPORARY DENTAL PROSTHESIS AND METHODS OF UTILIZING SAME

BACKGROUND

1. Field of the Invention

Embodiments of the present invention are generally related to embodiments of the present invention relate to a temporary dental prosthesis and methods of utilizing the same. More specifically, embodiments of the present invention relate to a dental prosthesis that may be quickly and easily set in a patient's mouth without the need for surgery or similar complex dental procedure.

2. Description of the Related Art

There are numerous situations that may arise wherein a person requires a dental prosthesis. Whether losing a tooth due to injury (e.g., in a car accident), to tooth decay requiring medical removal of the tooth, or by any of a variety of situations in between, it is not uncommon for an individual to lose a tooth.

As generally understood by those of ordinary skill in the art, once a tooth is removed by any means, the cavity is generally left open until it has an opportunity to heal. If the individual takes no action to clean and/or prevent food, bacteria, or other foreign substances from entering the cavity, a slew of medical issues may arise, causing significant health risks related to infection. Thus, a prosthesis is generally needed to provide an aesthetically pleasing appearance, as well as a medically useful guard against unwanted substances and to restore function.

However, due to the extremely high cost of permanent tooth replacement devices, many individuals having limited or fixed incomes and/or not having comprehensive dental insurance must either wait until sufficient funds become available, or alternatively, attempt temporary tooth constructions. Known temporary tooth constructions allow an individual to maintain their ordinary dental appearance when casually viewed, and may also serve as an adequate replacement until the more costly permanent solution to the problem can be acquired.

A downside of known temporary tooth constructions or replacement devices is the security and strength of the connection between the natural teeth remaining in the person's mouth and the temporary device. Known temporary devices can easily become dislodged when the person is eating, chewing, or merely not paying attention. Due to the size of these devices, the risk of swallowing or otherwise losing the device is apparent. Additionally, depending on the age of the person using the device, the act of accidentally swallowing the device may lead to choking or other dangerous consequences in the digestive tract.

In addition, known temporary dental prostheses require time to custom fit the device to the size and shape of a user's mouth. Such time could usually be a week or more, which means the user is left with either an open root and/or a medical bandage during that time. Beyond the obvious discomfort, many users may likely be significantly embarrassed, having to work or appear in social settings having a plainly visible missing tooth during that time.

As such, there is a need in the industry for an improved temporary dental prosthesis and methods of utilizing the same.

SUMMARY

Embodiments of the present invention are generally related to embodiments of the present invention relate to a temporary dental prosthesis and methods of utilizing the same. More specifically, embodiments of the present invention relate to a dental prosthesis that may be quickly and easily set in a patient's mouth without the need for surgery or similar complex dental procedure.

In one embodiment of the present invention, a temporary dental prosthesis comprises a primary body having a pair of axially positioned braces extending therefrom, the braces being connected to one another via an expansion means capable of extending and contracting the braces away from and towards the primary body, and an expansion control means for enabling the expansion means and controlling the expansion and contraction of the braces.

In another embodiment of the present invention, a temporary dental prosthesis comprises a primary body having a pair of axially positioned braces extending therefrom, the braces being connected to one another via an expansion means capable of extending and contracting the braces away from and towards the primary body, the expansion means extending through an axial bore extending through the temporary dental prosthesis, an expansion control means for enabling the expansion means and controlling the expansion and contraction of the braces, and a recessed portion for each of the braces.

In yet another embodiment of the present invention, a temporary dental prosthesis comprises a primary body having a pair of axially positioned braces extending therefrom, the braces being connected to one another via an expansion means having a shaft, and the shaft being fit into a cavity on a rear surface of each of the braces, the expansion means extending through an axial bore extending through the temporary dental prosthesis, and capable of extending and contracting the braces away from and towards the primary body, an expansion control means for enabling the expansion means and controlling the expansion and contraction of the braces, and a recessed portion for each of the braces.

BRIEF DESCRIPTION OF THE DRAWINGS

So the manner in which the above-recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments of embodiments encompassed within the scope of the present invention, and, therefore, are not to be considered limiting, for the present invention may admit to other equally effective embodiments, wherein:

FIG. 8 depicts a side view of a pad replacement tool for a temporary dental prosthesis in accordance with embodiments of the present invention; and FIG. 9 depicts a prospective view of a temporary dental prosthesis expansion tool in accordance with embodiments of the present invention.

Figure 1:
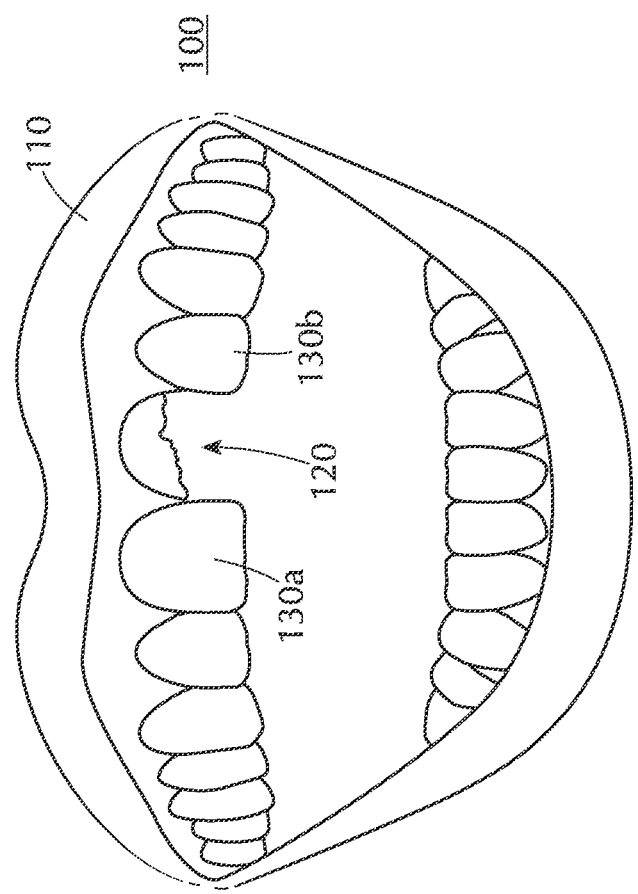
FIG. 1 depicts an individual's oral cavity having a missing tooth in accordance with embodiments of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present invention are generally related to embodiments of the present invention relate to a temporary dental prosthesis and methods of utilizing the same. More specifically, embodiments of the present invention relate to a dental prosthesis that may be quickly and easily set in a patient's mouth without the need for surgery or similar complex dental procedure.

FIG. 1 depicts an individual's oral cavity having a missing tooth in accordance with embodiments of the present invention. The oral cavity 100, as shown, comprises a mouth 110 having a vacant or missing tooth 120 situated adjacent to at least a first adjacent tooth 130a and optionally, a second adjacent tooth 130b. The vacant or missing tooth 120 may have been removed intentionally (e.g., due to necessary medical conditions) or accidentally (e.g., due to an accident or other non-voluntary situation).

Figure 2:
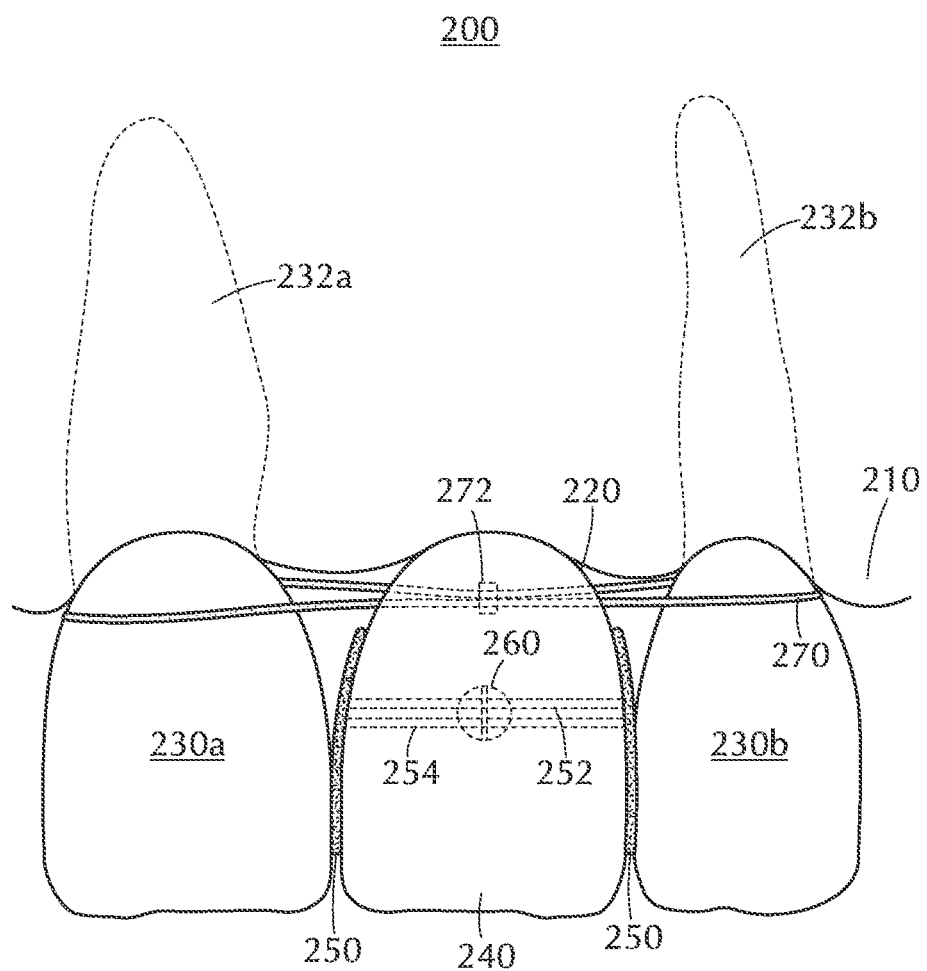
FIG. 2 depicts a schematic of a temporary dental prosthesis in its basic form in accordance with embodiments of the present invention.

FIG. 2 depicts a schematic of a temporary dental prosthesis in its basic form in accordance with embodiments of the present invention. As shown in the oral cavity segment 200, the vacant or missing tooth (i.e., cavity) 220 is positioned between at least a first adjacent tooth 230a and optionally, a second adjacent tooth 230b, both of which are firmly rooted with roots 232a and 232b, respectively, within the gum 210. Over the cavity 220, a temporary dental prosthesis 240 in accordance with embodiments of the present invention is provided therein. In many embodiments of the present invention, the temporary dental prosthesis 240 comprises any type of multi-sized and/or shaped primary body, representing the look of a natural human tooth.

Generally, a temporary dental prosthesis 240 comprises a primary body having a pair of axially positioned braces 250 or pads, which are positioned adjacent to the adjacent teeth 230a and 230b. In many embodiments, the braces 250 are either connection or in communication via an expansion means 252, passing through an axial bore 254, which is capable of pushing the braces 250 outward, away from the primary body of the temporary dental prosthesis 240 and towards the adjacent teeth 230a and 230b. The expansion means 252 is generally controlled by an expansion control means 260.

The braces 250 generally comprise a pliable material, suitable to retain a friction fit between the temporary dental prosthesis 240 and the adjacent teeth 230. In one embodiment, the braces 250 comprise a rubber, polymer or similar synthetic material. The shape of the braces 250 may depend upon the nature and positioning of the natural tooth being replaced and the adjacent teeth 230. It should be appreciated, any shape, size or contour of the temporary dental prosthesis 240 may be acceptable provided it meets the limitations set forth herein.

Optionally, in some embodiments, the temporary dental prosthesis 240 further comprises an additional retaining mechanism 270, which is affixed to the temporary dental prosthesis 240 via an attachment means 272. In one embodiment the retaining mechanism 270 comprises an elastic band, or pair of elastic bands, to extend from the temporary dental prosthesis 240 and go around at least one of the adjacent teeth 230. In some embodiments, the retaining mechanism 270 comprises a tying device (such as a rope, wire, etc.). In many embodiments, the retaining mechanism 270 acts as a safety device, to prevent the temporary dental prosthesis 240 from coming loose or being lost or swallowed.

The attachment means 272 may comprise any material or structure suitable for securing the retaining mechanism 270 to the temporary dental prosthesis 240. In one embodiment the attachment means 272 comprises a hook or loop extending off the back surface of the temporary dental prosthesis 240, and the retaining mechanism may be tied thereon or may pass therethrough. In another embodiment, the attachment means 272 comprises a chemical compound, such as an epoxy, adhesive, or the like, for securing the retaining mechanism 270 to the temporary dental prosthesis 240.

The temporary dental prosthesis 240 may be made from any material suitable for embodiments of the present invention. In many embodiments, the temporary dental prosthesis 240 is made of any of the materials accepted by American Dental Association (ADA) and/or the American College of Prosthodontics, as being suitable for dental prostheses. In some embodiments of the present invention, the temporary dental prosthesis 240 is made from any of porcelain, ceramics, acrylics, polymers, glass, wood, precious metals, or combinations thereof.

Figure 3A:
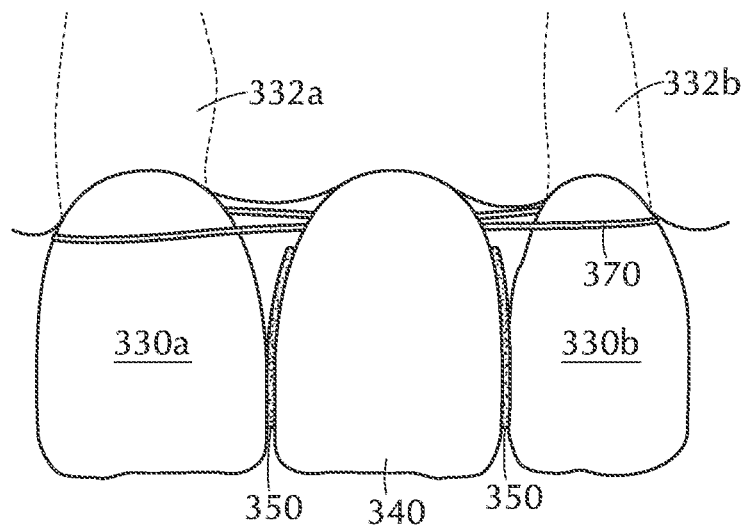
FIGS. 3A and 3B depict a front and rear view, respectively, of a temporary dental prosthesis for the front teeth in a user's mouth in accordance with embodiments of the present invention.
Figure 3B:
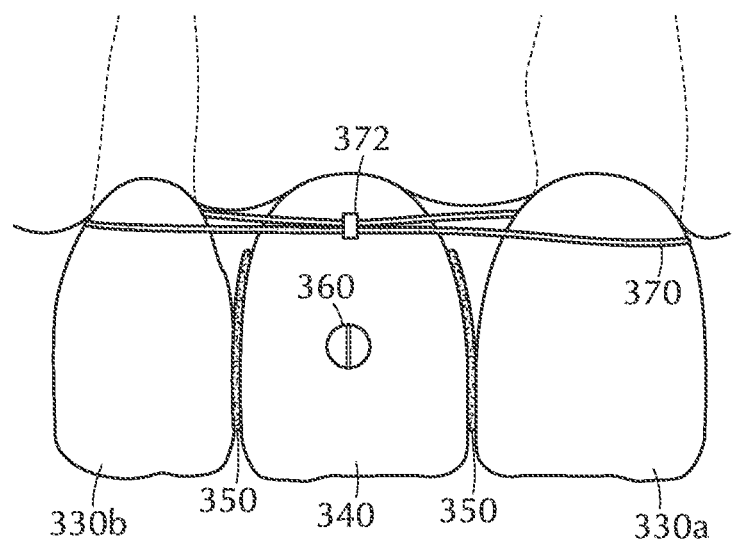

FIGS. 3A and 3B depict a front and rear view, respectively, of a temporary dental prosthesis in a user's mouth in accordance with embodiments of the present invention, as it would visibly appear to someone looking at the user's mouth. As shown in FIG. 3A, when viewing the front of a temporary dental prosthesis 340, none of the internal components can be viewed (i.e., the temporary dental prosthesis appears smooth to anyone who casually views the individual's oral cavity. As such, from a front view, only the temporary dental prosthesis 340, a portion of the braces 350, and the portion of the optional retaining mechanism 370 around the gum line of each of the adjacent teeth 330, are visible.

As shown in FIG. 3B, in many embodiments, the rear view of the temporary dental prosthesis 340 reveals similar components as the front view supra, as well as the expansion control means 360, a more prominent portion of the optional retaining mechanism 370, and the associated attachment means 372. Although the expansion control means 360 is positioned on the rear surface of the temporary dental prosthesis 340, it should be appreciated by alternative embodiments, the placement of the expansion control means 360 may be anywhere along the outer surface of the temporary dental prosthesis 340 suitable for embodiments of the present invention.

Figure 4A:
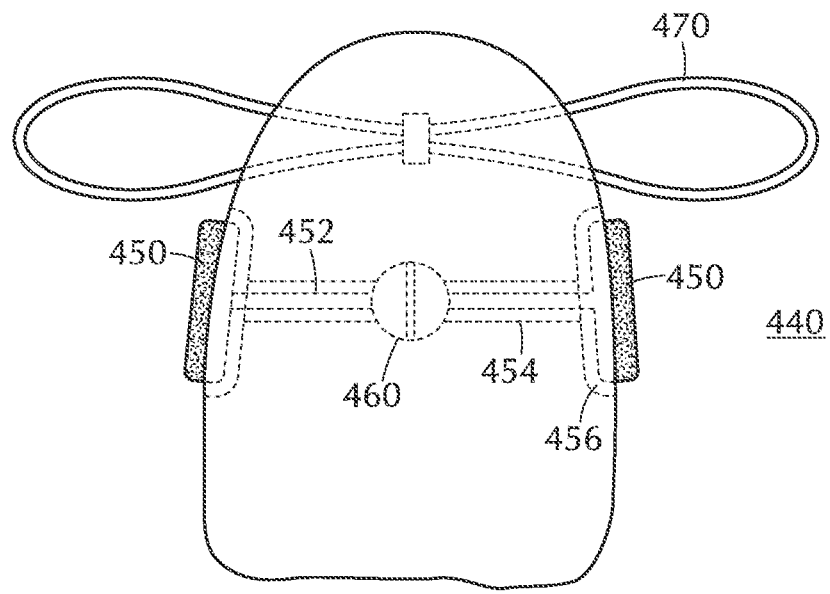
FIGS. 4A and 4B depict a front and a rear view, respectively, of a temporary dental prosthesis for the front teeth in accordance with embodiments of the present invention.
Figure 4B:
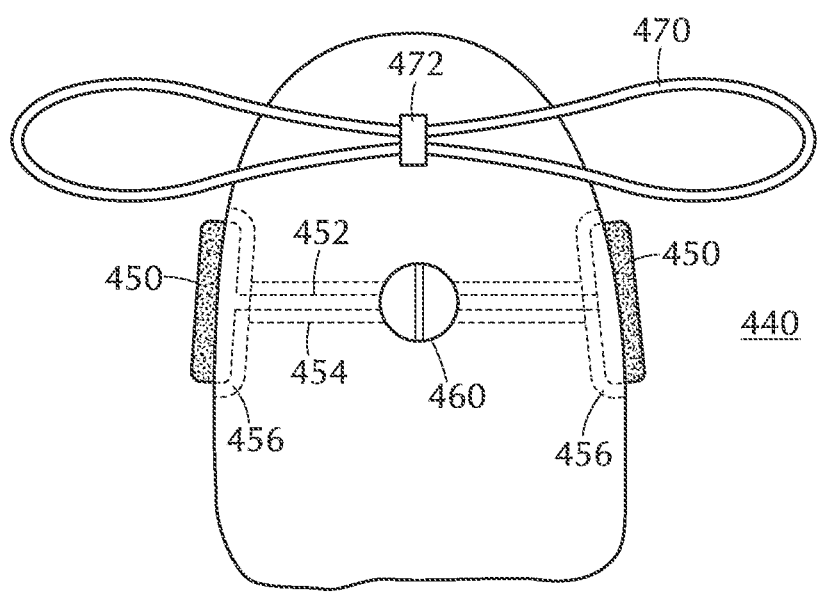

FIGS. 4A and 4B depict a front and a rear view, respectively, of a temporary dental prosthesis in accordance with embodiments of the present invention. In one embodiment of the present invention, a temporary dental prosthesis 440 generally comprises a pair of axially opposed braces 450 connected via an expansion means 452, which may extend through an axial bore 454 extending through the temporary dental prosthesis 4. In many embodiments, the expansion means 452 may be controlled by an expansion control means 460. As shown in the figure, the temporary dental prosthesis 440 may additionally comprise a retaining mechanism 470 and an associated attachment means 472.

Optionally, a temporary dental prosthesis 440 may comprise a recessed portion 456 for each of the braces 450. In such embodiments, the recessed portions 456 may comprise voids on the sides of the temporary dental prosthesis 440 in which the braces 450 may be stored when in a fully collapsed (or un-expanded) position. Such recessed portions would allow for the temporary dental prosthesis 440 to be positioned within a tight fitting space between two adjacent teeth.

Figure 5A:
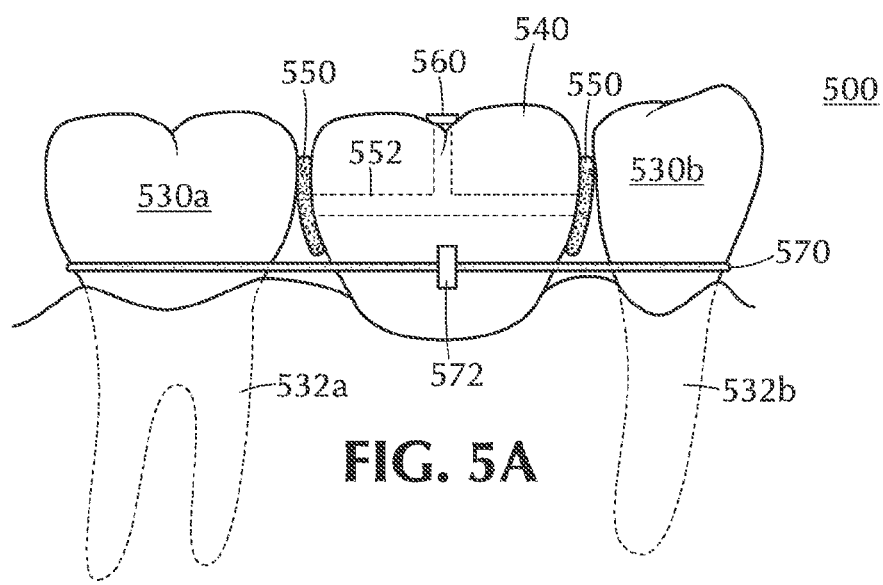
FIGS. 5A and 5B depict a front and a top view, respectively, of a temporary dental prosthesis for the back teeth in a user's mouth in accordance with embodiments of the present invention.
Figure 5B:
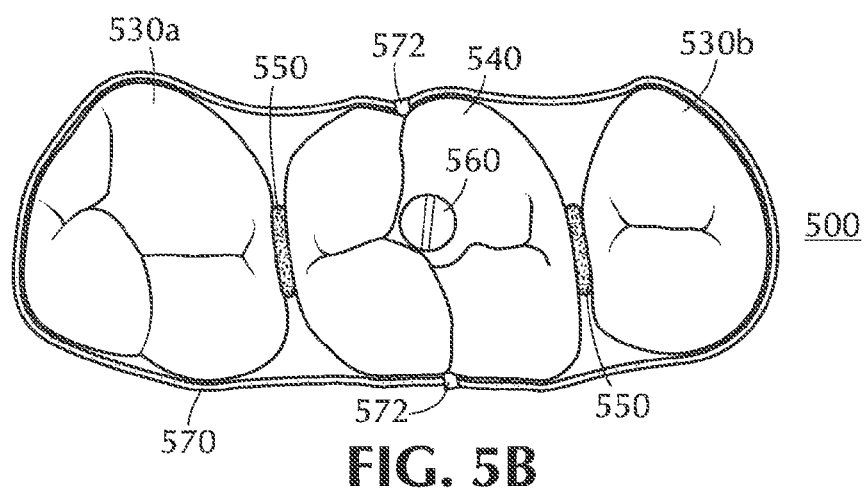

FIGS. 5A and 5B depict a front and a top view, respectively, of a temporary dental prosthesis in a user's mouth in accordance with embodiments of the present invention. As shown in the Figure, within an individual's oral cavity 500, an individual's gums support a first adjacent tooth 530a and a second adjacent tooth 532b, both of which have roots 532a and 532b embedded within the gums, respectively. Between the first and second adjacent teeth 530a and 532b is a temporary dental prosthesis 540 in accordance with embodiments of the present invention.

Similar to the embodiments described above, the temporary dental prosthesis 540 generally comprises a primary body having a pair of axially positioned braces 550, which are positioned adjacent to the adjacent teeth 530a and 530b. In many embodiments, the braces 550 are either connection or in communication via an expansion means (not shown), which is capable of pushing the braces 550 outward, and is controlled by an expansion control means 560.

In the embodiment depicted, the expansion control means is provided on the top surface of the tooth, as more clearly portrayed in FIG. 5B. In certain embodiments, particularly where the temporary dental prosthesis 540 is replacing a natural molar, it may be more convenient to provide the expansion control means 560 on the top surface of the tooth. However, in alternative embodiments of the present invention, the expansion control means 560 could also be provided on any other accessible surface of the temporary dental prosthesis 540.

Figure 6:
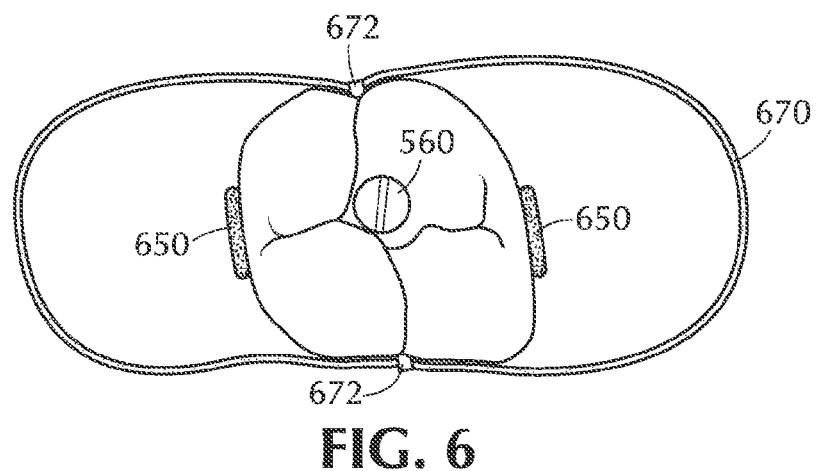
FIG. 6 depicts a top view of a temporary dental prosthesis for the back teeth in accordance with embodiments of the present invention.

FIG. 6 depicts a top view of a temporary dental prosthesis in accordance with embodiments of the present invention. The temporary dental prosthesis is similar to those described above, such that it comprises a pair of axially opposed braces 650 and an expansion control means 560 for operating the axial movement of the braces 650. In addition, the temporary dental prosthesis may optionally comprise a retaining mechanism 670 passing the entire way around the temporary dental prosthesis, and passing through at least one attachment means 672 for keeping the retaining mechanism 670 attached thereto. As shown in the exemplary embodiment in the Figure, two or more attachment means 672 may be provided, particularly where the retaining mechanism 670 is intended to pass around both a front and back surface of the temporary dental prosthesis.

Figure 7A:
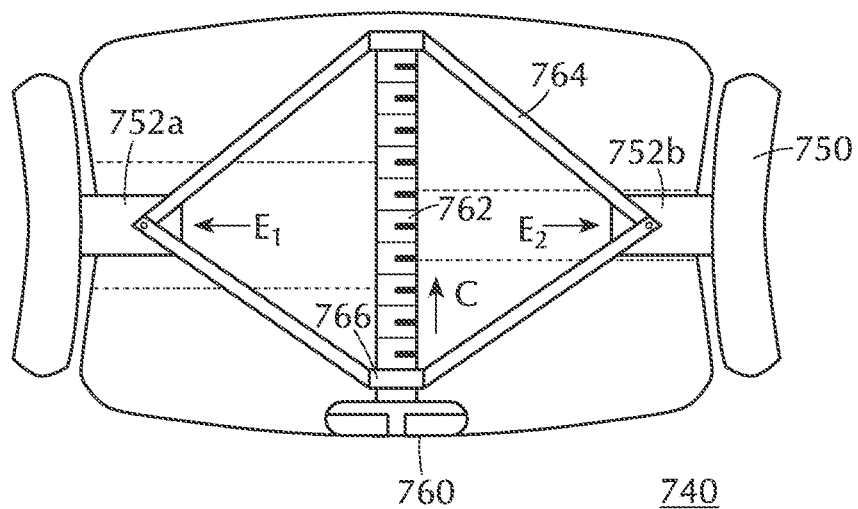
FIG. 7A depicts a cross-sectional view of a temporary dental prosthesis for one exemplary embodiment in accordance with embodiments of the present invention.

FIG. 7A depicts a cross-sectional view of a temporary dental prosthesis for one exemplary embodiment in accordance with embodiments of the present invention. The temporary dental prosthesis 740 shown in the Figure comprises one exemplary embodiment of an expansion means 752 and expansion control means 760. In the exemplary embodiment, the expansion means 752 comprises a mechanical assembly having an anchor screw design (e.g., similar to a drywall screw anchor). In such an embodiment, the anchor screw design comprises a threaded shaft 762, at least two pairs of angled, rotatable arms 764, the joint of each pair of arms meeting at an axially positioned shaft connected to a brace 750. The anchor screw design further provides a slideable washer 766 connected to a first end of the threaded shaft 762 and to one end of each of one arm of the two pairs of arms. The slideable washer 766 may have threads on an inner surface thereof, such that the washer may move along the threads as the threaded shaft 762 is rotated. Generally speaking, in such an embodiment, the opposing end of each pair of arms is rotatable about the second end of the threaded shaft 762, but are not slideable up/down the shaft.

In operation, by engaging the expansion control means 760, which imparts rotational motion upon the threaded shaft 762, the slideable washer 766 begins to move down the threaded shaft 762 in direction C. As the slideable washer 766 moves along direction C, each of the axially positioned shafts 752a and 752b move along directions $E_1$ and $E_2$, respectively. As the axially positioned shafts 752a and 752b move outward, the braces 750 move outward as well, and can create a tensile force with an adjacent tooth, keeping the temporary dental prosthesis in place.

Figure 7B:
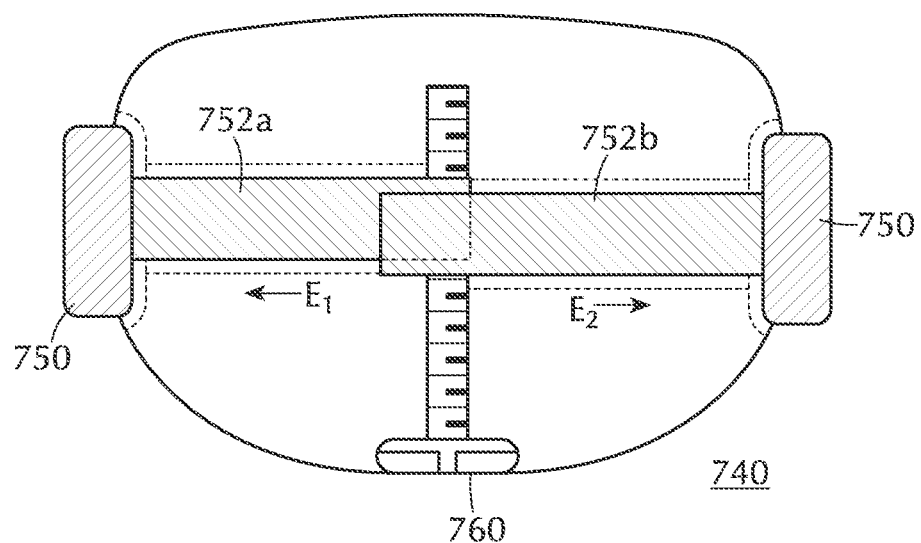
FIG. 7B depicts a cross-sectional view of a temporary dental prosthesis for another exemplary embodiment in accordance with embodiments of the present invention.

FIG. 7B depicts a cross-sectional view of a temporary dental prosthesis for another exemplary embodiment in accordance with embodiments of the present invention. Similar to the embodiment shown in FIG. 7A, the temporary dental prosthesis 740 of FIG. 7B comprises one exemplary embodiment of an expansion means 752 and expansion control means 760. In the exemplary embodiment, the expansion means 752 comprises a mechanical assembly having a rack and pinion design. In such an embodiment, the rack and pinion design comprises a threaded shaft acting as a pinion gear, controlled by the expansion control means 760, and two expansion means 752a and 752b which act as racks. In one embodiment, in operation, upon clockwise rotation of the expansion control means 760, the expansion means 752a and 752b will be pushed outward in the direction of E1 and E2, respectively, by virtue of teeth thereon (i.e., as commonly possessed by a rack device in a rack and pinion system). In such an embodiment, the expansion means 752a may be positioned above the threaded shaft of the expansion control means 760, and the expansion means 752b may be positioned below the threaded shaft of the expansion control means 760.

Alternatively, any number of expansion means 752 and expansion control means 760 may be provided to achieve the same or similar result for other embodiments of the present invention. Suitable expansion means 752 and expansion control means 760 structures may include any type of mechanical systems (e.g., screw and gear systems, etc.), hydroelectric/pressurized systems (e.g., using pressurized fluids to expand the braces), electronic/electro-mechanical systems (e.g., powered systems for expanding or releasing the braces), or the like.

FIG. 8 depicts a side view of a pad replacement tool for a temporary dental prosthesis in accordance with one exemplary embodiment of the present invention. In some embodiments, the brace 850 may be provided in the form of a removable pad, which can be cleaned, replaced, or adjusted if a better fit is needed. As shown in the Figure, a shaft of the expansion means 852 may generally be positioned into the brace 850 into cavity 853. In some embodiments, the expansion means 852 may be form and friction fitted into the cavity 853. However, in certain embodiments, any of a mechanical (e.g., threads, fasteners, etc.), chemical (e.g., adhesives), or alternative (e.g., magnetic, etc.) connection means may be provided.

In such embodiments of the present invention, on the front surface of the brace 850, at least one removal recessed portions 880 is provided. Generally, the removal recessed portion 880 is a cavity or void having little to no impact on the fit of the brace 850 against an adjacent tooth, and can be fitted to a pad removal tool 890 in accordance with embodiments of the present invention.

As shown in the Figure, the pad removal tool 890 comprises a mechanical tool having at least a handle rotatably connected via a hinge 896 to a substantially rigid arm 894 having at least one fitted removal tine 892. The removal time 892 is generally shaped to accommodate the removal recessed portion 880 of the brace 850. By utilizing the pad removal tool 890 the temporary dental prosthesis 840 may be handled in a much more careful manner, and the risk of losing or incorrectly placing a pad on the extension means is significantly less than attempting to handle by hand.

FIG. 9 depicts a prospective view of a temporary dental prosthesis expansion tool in accordance with embodiments of the present invention. In many embodiments of the present invention, the expansion control means may be provided in the form of a screw head. As such, a temporary dental prosthesis expansion tool 900 matching the same structural design as the screw head must be utilized to engage the expansion control means. As shown in the Figure, a temporary dental prosthesis expansion tool generally comprises a handle 901 having a shaft 902 extending therefrom. At the end of the shaft 902, a head 903 is provided. Generally, the shape of the head 903 matches the inverse design of the expansion control means. In several embodiments, however, the head 903 comprises a substantially similar design to a traditional flathead or Phillips head screwdriver. Other well-known shaped screw heads may be utilized as well—e.g., a star-shaped head, a hexagonal shaped head, etc.

Optionally, in some embodiments, the temporary dental prosthesis expansion tool 900 comprises a support bore 904 for allowing a support string 905 to pass through the handle 901. Because of the size of the temporary dental prosthesis expansion tool 900, the support string 905 allows the user to ensure the temporary dental prosthesis expansion tool 900 does not slip and get swallowed. In view of the nature of the embodiments of the present invention, in certain embodiments, the support string 905 comprises dental floss. In other embodiments, any type of fiber-based material may be suitable.

Although embodiments of the present invention are primarily directed to a single tooth prosthesis, it should be appreciated by further embodiments, that the temporary dental prosthesis may comprise a plurality of artificial teeth assembled in a row, to replace adjacent missing teeth in a user's mouth. In such an embodiment, the features described herein may likely be present, and the plurality of artificial teeth may be considered as a single body, such that the components of embodiments of the present invention (e.g., the braces, the extension control means, etc.) may operate through the plurality of artificial teeth as if they were a single artificial tooth. In such embodiments, however, certain elements, such as a retaining mechanism, may exist in the form of two elastics, each having respective attachment means positioned on opposing ends of a backside of the temporary dental prosthesis.

While the foregoing is directed to embodiments of the present invention, other and further embodiments of the invention may be devised without departing from the basic scope thereof. It is also understood that various embodiments described herein may be utilized in combination with any other embodiment described, without departing from the scope contained herein. In addition, embodiments of the present invention may be further scalable, as particular applications may require.

What is claimed is:

1. A temporary dental prosthesis comprising:
    a primary body having a tooth shape, the primary body adapted to be inserted between natural teeth, the primary body having a pair of axially positioned braces extending therefrom, the braces being connected to one another via an expansion means capable of extending and contracting the braces away from and towards the primary body;
    an expansion control means positioned on a lingual side of the primary body, the expansion control means for enabling the expansion means and controlling the expansion and contraction of the braces; and
    a retaining mechanism attached to an exterior surface of the primary body and adapted to surround the natural teeth when in use, the retaining mechanism comprising one of an elastic band, a pair of elastic bands, or a tying device, the retaining mechanism spaced vertically away from the axially positioned braces.

2. The temporary dental prosthesis of claim 1, wherein the temporary dental prosthesis comprises at least one of porcelain, ceramic, acrylic, polymer, glass, wood, precious metal, or combinations thereof.

3. The temporary dental prosthesis of claim 1, wherein the expansion means extends through an axial bore extending through the temporary dental prosthesis.

4. The temporary dental prosthesis of claim 1, further comprising a recessed portion for each of the braces.

5. The temporary dental prosthesis of claim 1, wherein the expansion means comprises at least one of a mechanical system, a hydroelectric system, an electronic system, or combinations thereof.

6. The temporary dental prosthesis of claim 1, further comprising an attachment means attaching the retaining mechanism to the primary body, the attachment means comprising at least one of a hook or a loop extending from the lingual side of the primary body, or a chemical compound for securing the retaining mechanism to the primary body.

7. A temporary dental prosthesis comprising:
    a primary body having a tooth shape, the primary body adapted to be inserted between natural teeth, the primary body having a pair of axially positioned braces extending therefrom, the braces being connected to one another via an expansion means capable of extending and contracting the braces away from and towards the primary body, the expansion means extending through an axial bore extending through the temporary dental prosthesis;
    an expansion control means for enabling the expansion means and controlling the expansion and contraction of the braces;
    a recessed portion for each of the braces; and
    a retaining mechanism attached to an exterior surface of the primary body and adapted to surround the natural teeth when in use, the retaining mechanism comprising one of an elastic band, a pair of elastic bands, or a tying device, the retaining mechanism spaced vertically away from the axially positioned braces.

8. The temporary dental prosthesis of claim 7, wherein the expansion control means is positioned on one of a lingual surface of the primary body or an occlusal surface of the primary body.

9. The temporary dental prosthesis of claim 7, wherein the expansion means comprises at least one of a mechanical system, a hydroelectric system, an electronic system, or combinations thereof.

\* \* \* \* \*